(12) United States Patent
Fell et al.

(10) Patent No.: US 8,128,697 B2
(45) Date of Patent: Mar. 6, 2012

(54) PROPORTIONED SURGICALLY IMPLANTABLE KNEE PROSTHESIS

(76) Inventors: Barry M. Fell, Hummelstown, PA (US); Richard H. Hallock, Hummelstown, PA (US)

(*) Notice: Subject to any disclaimer, the term of this patent is extended or adjusted under 35 U.S.C. 154(b) by 0 days.

(21) Appl. No.: 12/574,830

(22) Filed: Oct. 7, 2009

(65) Prior Publication Data

US 2010/0076562 A1 Mar. 25, 2010

Related U.S. Application Data

(63) Continuation of application No. 12/045,627, filed on Mar. 10, 2008, now abandoned, which is a continuation of application No. 10/232,608, filed on Aug. 30, 2002, now Pat. No. 7,341,602, which is a continuation of application No. 09/934,364, filed on Aug. 21, 2001, now abandoned, which is a continuation-in-part of application No. 09/664,939, filed on Sep. 19, 2000, now Pat. No. 6,558,421, which is a continuation of application No. 09/297,943, filed as application No. PCT/US99/07309 on Apr. 2, 1999, now Pat. No. 6,206,927.

(51) Int. Cl.
 *A61F 2/38* (2006.01)
(52) U.S. Cl. .................. 623/14.12; 623/20.29; 623/20.3
(58) Field of Classification Search .... 623/20.14–20.36, 623/14.12
See application file for complete search history.

(56) References Cited

U.S. PATENT DOCUMENTS

| | | |
|---|---|---|
| 3,869,731 A | 3/1975 | Waugh et al. |
| 4,052,753 A | 10/1977 | Dedo |
| 4,207,627 A | 6/1980 | Cloutier |
| 4,344,193 A | 8/1982 | Kenny |
| 4,385,404 A | 5/1983 | Sully et al. |
| 4,446,578 A | 5/1984 | Perkins et al. |
| 4,502,161 A | 3/1985 | Wall |
| 4,722,948 A | 2/1988 | Sanderson |

(Continued)

FOREIGN PATENT DOCUMENTS

DE 3840470 A1 6/1990

(Continued)

OTHER PUBLICATIONS

Wheeler, J.; "Little Device Could Pack a Big Punch"; Sulzer Medica Journal, Feb. 2000, pp. 16-17.

(Continued)

*Primary Examiner* — David H Willse
*Assistant Examiner* — Javier Blanco
(74) *Attorney, Agent, or Firm* — Brooks Kushman P.C.

(57) ABSTRACT

A unicompartmental knee prosthesis for implantation into a knee joint includes a body having a substantially elliptical shape in plan and a pair of contoured opposed faces including a first face and a second face, the second face including a concave surface. The prosthesis is free of fixation to a permanent location within the knee joint compartment. A peripheral edge extends between the faces and has a first side, a second side opposite the first side, and a first end and a second end opposite the first end, the body including a cusp comprising a reverse curve downward from to the first face at one of the first and second ends. A first dimension D is defined by the first end and the second end, and a second dimension F is defined by the first side and the second side. A coordinate system origin (CSO) is at an intersection of D and F, the body including a material thickness at the CSO, where the dimension F is from about 0.25 to about 1.5 of the dimension D.

15 Claims, 4 Drawing Sheets

U.S. PATENT DOCUMENTS

| | | | |
|---|---|---|---|
| 4,808,185 A | 2/1989 | Penenberg et al. |
| 4,880,429 A | 11/1989 | Stone |
| 4,919,667 A | 4/1990 | Richmond |
| 5,007,934 A | 4/1991 | Stone |
| 5,067,964 A | 11/1991 | Richmond et al. |
| 5,109,589 A | 5/1992 | Cramer et al. |
| 5,158,574 A | 10/1992 | Stone |
| 5,171,322 A | 12/1992 | Kenny |
| 5,263,987 A | 11/1993 | Shah |
| 5,278,201 A | 1/1994 | Dunn et al. |
| 5,344,459 A | 9/1994 | Swartz |
| 5,387,240 A | 2/1995 | Pottenger et al. |
| 5,480,446 A | 1/1996 | Goodfellow et al. |
| 5,496,682 A | 3/1996 | Quadir et al. |
| 5,549,688 A | 8/1996 | Ries et al. |
| 5,556,432 A | 9/1996 | Kubein-Meesenburg et al. |
| 5,683,468 A | 11/1997 | Pappas |
| 5,702,466 A | 12/1997 | Pappas et al. |
| 5,725,584 A | 3/1998 | Walker et al. |
| 5,795,353 A | 8/1998 | Felt |
| 5,871,541 A | 2/1999 | Gerber |
| 5,888,220 A | 3/1999 | Felt et al. |
| 5,964,808 A | 10/1999 | Blaha et al. |
| 6,206,927 B1 | 3/2001 | Fell et al. |
| 6,558,421 B1 | 5/2003 | Fell et al. |
| 6,679,914 B1 | 1/2004 | Gabbay |
| 6,855,165 B2 | 2/2005 | Fell et al. |
| 6,866,684 B2 | 3/2005 | Fell |
| 6,911,044 B2 | 6/2005 | Fell |
| 6,923,831 B2 | 8/2005 | Fell |
| 6,966,928 B2 | 11/2005 | Fell |
| 7,297,161 B2 | 11/2007 | Fell |
| 7,338,524 B2 | 3/2008 | Fell et al. |
| 7,341,602 B2 | 3/2008 | Fell et al. |

FOREIGN PATENT DOCUMENTS

| | | |
|---|---|---|
| FR | 2635678 A1 | 3/1990 |
| FR | 2700263 A1 | 7/1994 |
| FR | 2747914 A1 | 10/1997 |
| GB | 2312166 A | 10/1997 |

OTHER PUBLICATIONS

Hollister, Anne M. M.D., et al., The Axes of Rotation of the Knee, Clinical Orthopaedics and Related Research, No. 290, pp. 259-268.

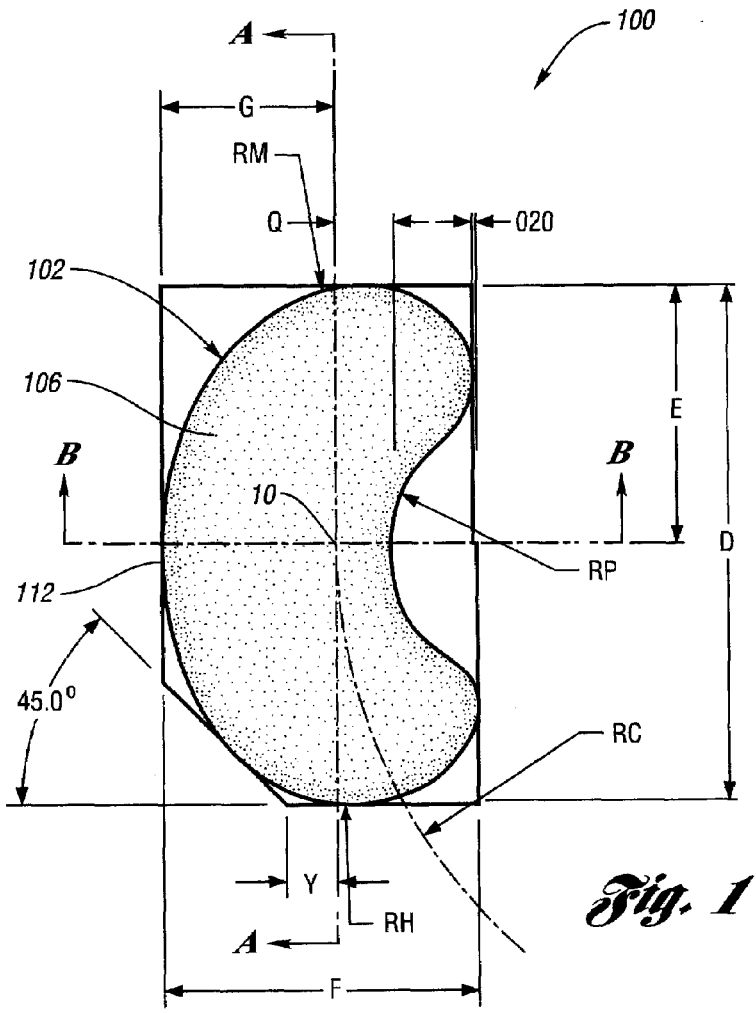
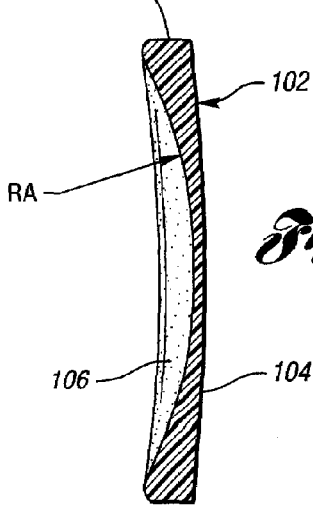
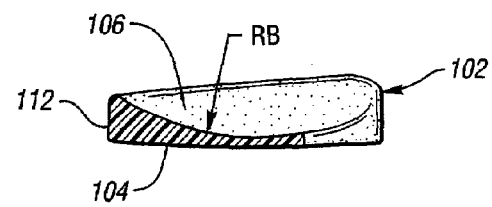
Fig. 1
Fig. 2
Fig. 3

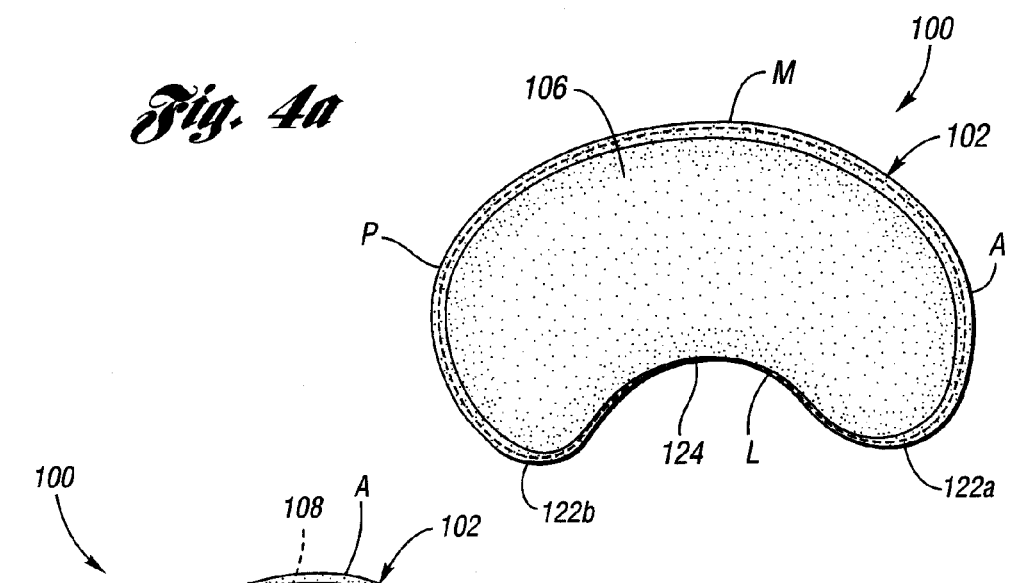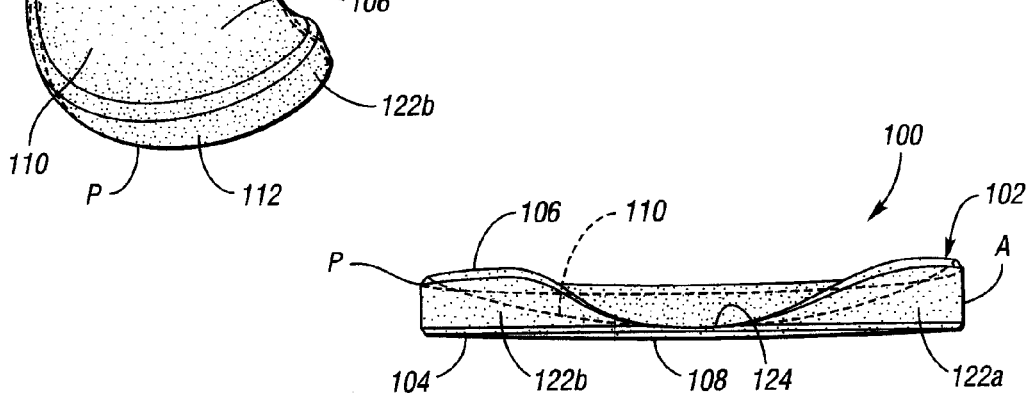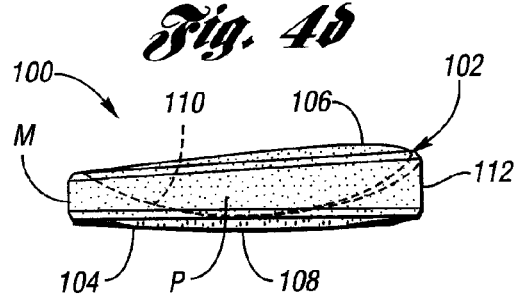

PROPORTIONED SURGICALLY IMPLANTABLE KNEE PROSTHESIS

CROSS-REFERENCE TO RELATED APPLICATIONS

This application is a continuation of U.S. application Ser. No. 12/045,627, filed Mar. 10, 2008, now abandoned, which is a continuation of U.S. application Ser. No. 10/232,608, filed Aug. 30, 2002, now U.S. Pat. No. 7,341,602, which is a continuation of U.S. application Ser. No. 09/934,364, filed Aug. 21, 2001, now abandoned, which is a continuation-in-part of U.S. application Ser. No. 09/664,939, filed Sep. 19, 2000, now U.S. Pat. No. 6,558,421, which is a continuation of U.S. application Ser. No. 09/297,943, filed May 10, 1999, now U.S. Pat. No. 6,206,927, which is the National Stage Entry of PCT/US99/07309 filed Apr. 2, 1999, each of which are incorporated by reference herein.

BACKGROUND OF THE INVENTION

1. Field of the Invention

The present invention pertains to prosthetic devices. More particularly, the invention pertains to knee joint prostheses which may be surgically implanted between the femoral condyle and tibial plateau of the knee joint.

2. Background Art

Articular cartilage and meniscal cartilage provide the mobile weight bearing surfaces of the knee joint. Damage to these surfaces is generally due to genetic predisposition, trauma, and/or aging. The result is usually the development of chondromalacia, thinning and softening of the articular cartilage, and degenerative tearing of the meniscal cartilage. Various methods of treatment are available to treat these disease processes. Each option usually has specific indications and is accompanied by a list of benefits and deficiencies that may be compared to other options.

The healthy knee joint has a balanced amount of joint cartilage across the four surfaces of this bi-compartmental joint (medial femoral condyle, medial tibial plateau, lateral femoral condyle and lateral tibial plateau). In patients with osteoarthritis, degenerative process typically leads to an asymmetric wear pattern that leaves one compartment with significantly less articular cartilage covering the distal portions (or weight bearing area) of the tibia and femur than the other compartment. Most commonly, the medial compartment of the knee joint is affected more often than the lateral compartment.

As the disease progresses, large amounts of articular cartilage are worn away. Due to the asymmetric nature of the erosion, the alignment of the mechanical axis of rotation of the femur relative to the tibia becomes tilted down towards the compartment which is suffering the majority of the erosion. The result is a Varus (bow-legged) deformity in the case of a medial compartment disease predominance, or a Valgus (knock-kneed) deformity in the case of lateral compartment disease predominance. Factors such as excessive body weight, previous traumatic injury, knee instability, the absence of the meniscus and genetic predisposition, all affect the rate of the disease.

The disease is usually defined in stages of Grade I through V, with Grade III revealing significant articular cartilage loss, Grade IV revealing some eburnation of the subchondral bone, and Grade V detailing both significant articular loss and bone loss.

It is important to understand that the disease manifests itself as periodic to continuous pain that can be quite uncomfortable for the patient. The cause of this pain is subject to many opinions but it is apparent that, as the joint compartment collapses, the collateral ligament on the side of the predominant disease becomes increasingly slack (like one side of a pair of loose suspenders), and the tibial and femoral axes move, for example, from a Varus to a Valgus condition. This increases the stress on the opposing collateral ligament (and cruciate ligaments as well) and shifts the load bearing function of this bi-compartmental joint increasingly towards the diseased side. This increasing joint laxity is suspected of causing some of the pain one feels. In addition, as the bearing loads are shifted, the body responds to the increased loading on the diseased compartment with an increased production of bony surface area (osteophytes) in an attempt to reduce the ever-increasing areal unit loading. All of this shifting of the knee component geometry causes a misalignment of the mechanical axis of the joint. The misalignment causes an increase in the rate of degenerative change to the diseased joint surfaces causing an ever-increasing amount of cartilage debris to build up in the joint, further causing joint inflammation and subsequent pain.

Currently, there is a void in options used to treat the relatively young patient with moderate to severe chondromalacia involving mainly one compartment of the knee. Current treatments include NSAIDs, cortisone injections, hyaluronic acid (HA) injections and arthroscopic debridement. Some patients cannot tolerate or do not want the risk of potential side effects of NSAIDs. Repeated cortisone injections actually weaken articular cartilage after a long period of time. HA has shown promising results but is only a short term solution for pain. Arthroscopic debridement alone frequently does not provide long lasting relief of symptoms. Unfortunately, the lack of long term success of these treatments leads to more invasive treatment methods. Osteochondral allografts and microfracture techniques are indicated for small cartilage defects that are typically the result of trauma. These procedures are not suitable for addressing large areas of degeneration. In addition, osteochondral allografts can only be used to address defects on the femoral condyle. Tibial degeneration can not be addressed with this technique. High tibial osteotomy (HTO) corrects the varus malalignment between the tibia and femur but, because it is performed below the joint line, it does not fill the cartilage void or re-tension the medial collateral ligament (MCL). Removing bone and changing the joint line does not complicate the conversion to total knee arthroscopy (TKA). However, an HTO does leave a hard sclerotic region of bone which is difficult to penetrate making conversion to a total knee replacement (TKR) technically challenging. Unicompartmental and bicompartmental total knee replacements resect significant amounts of bone and, if performed on younger patients, will likely require revision surgery as they age. Revision total knee replacement surgery is usually extensive and results in predictably diminished mechanical life expectancy. Therefore, it is best to delay this type of bone resecting surgery as long as possible.

The only true solution is to rebuild the defective joint by "filling" the joint space with more articular bearing material through a complete resurfacing of the existing femoral condyle and tibial plateau. By replacing the original cartilage to its pre-diseased depth, the joint mechanical axis alignment is restored to its original condition. Unfortunately, these natural articular materials and surgical technology required to accomplish this replacement task do not yet exist.

Currently, replacement of the existing surfaces, with materials other than articular cartilage, is only possible with a total or uni-condylar knee replacement, and these procedures require removal of significant amounts of the underlying bone structure.

The alternative method is to fill the joint space with a spacer that replaces the missing articular materials. This spacer should also provide an anatomically correct bearing surface for both the tibial and femoral surface (U.S. Pat. No. 6,206, 927).

Attaching a new bearing surface to the femoral condyle is technically challenging and was first attempted, with limited success, over 40 years ago with the MGH (Massachusetts General Hospital) knee. Like a dental crown, it covered both femoral condyles with Vitallium (CoCr) and would bear against the existing tibial plateau.

Tibial covering devices such as the McKeever, Macintosh and Townley tibial tray, maintained the existing femoral surface as the bearing surface, but like the MGH knee, all required significant bone resection, thus making them less than ideal solutions as well.

These devices also made no particular attempt to match the patient's specific femoral or tibial geometry thus reducing their chances for optimal success. Because these devices were made of CoCr, which has different visco-elastic and wear properties from the natural articular materials, any surface geometry which did not closely match the bearing surface of the tibia or femur, could cause premature wear of the remaining cartilage due to asymmetric loading.

Newer materials technologies in development include filling the joint space by injecting polyurethane (U.S. Pat. No. 5,795,353) into the joint and anchoring it with holes drilled into the tibial plateau. Others include a series of polymeric materials such as PVA Hydrogels in a titanium mesh as described by Chang et al, "Historical Comparison of Tibial Articular Surfaces Against Rigid Materials And Artificial Articular Cartilage," Journal of Biomedical Material Research, 37, 51-59, 1997, biodegradable anhydride prepolymers that can be cross linked with irradiation by UV light (U.S. Pat. No. 5,902,599) and in-vivo grown articular chondrocytes in a collagen fiber or other bio-compatible scaffold (U.S. Pat. No. 5,158,574). Other low surface energy materials, such as low temperature isotropic (LTI) pyrolitic carbon, have been investigated as bearing surfaces as well.

All of these techniques are limited by one's ability to first of all fashion these materials in a conformal fashion to replicate the existing knee geometry, while at the same time, maintaining their location within the joint while further being able to survive the mechanical loading conditions of the knee.

Therefore, what is needed is a uni-compartmental interpositional spacer which, by effectively replacing worn articular material, restores normal joint alignment without requiring any bone resection or any means of bone fixation and provides an anatomically correct bearing surface for the femoral condyle to articulate against.

SUMMARY OF THE INVENTION

According to one embodiment, an implantable knee prosthesis for unicompartmental implantation into a knee joint includes a body having a substantially elliptical shape in plan and a pair of contoured opposed faces including a convex face and a concave face. A peripheral edge extends between the faces and includes a first side, a second side opposite the first side, a first end and a second end opposite the first end. A first dimension D is defined by the first end and the second end. A second dimension F is defined by the first side and the second side. The dimension F is from about 0.25 to about 1.5 of the dimension D.

BRIEF DESCRIPTION OF THE DRAWINGS

FIG. 1 is a plan view illustrating an embodiment of an implantable knee prosthesis;

FIG. 2 is a cross-sectional view taken along the line A-A of FIG. 1;

FIG. 3 is a cross-sectional view taken along line B-B of FIG. 1;

FIGS. 4a-4d illustrate several views of an embodiment of the device;

DETAILED DESCRIPTION OF THE INVENTION

Figure 5:
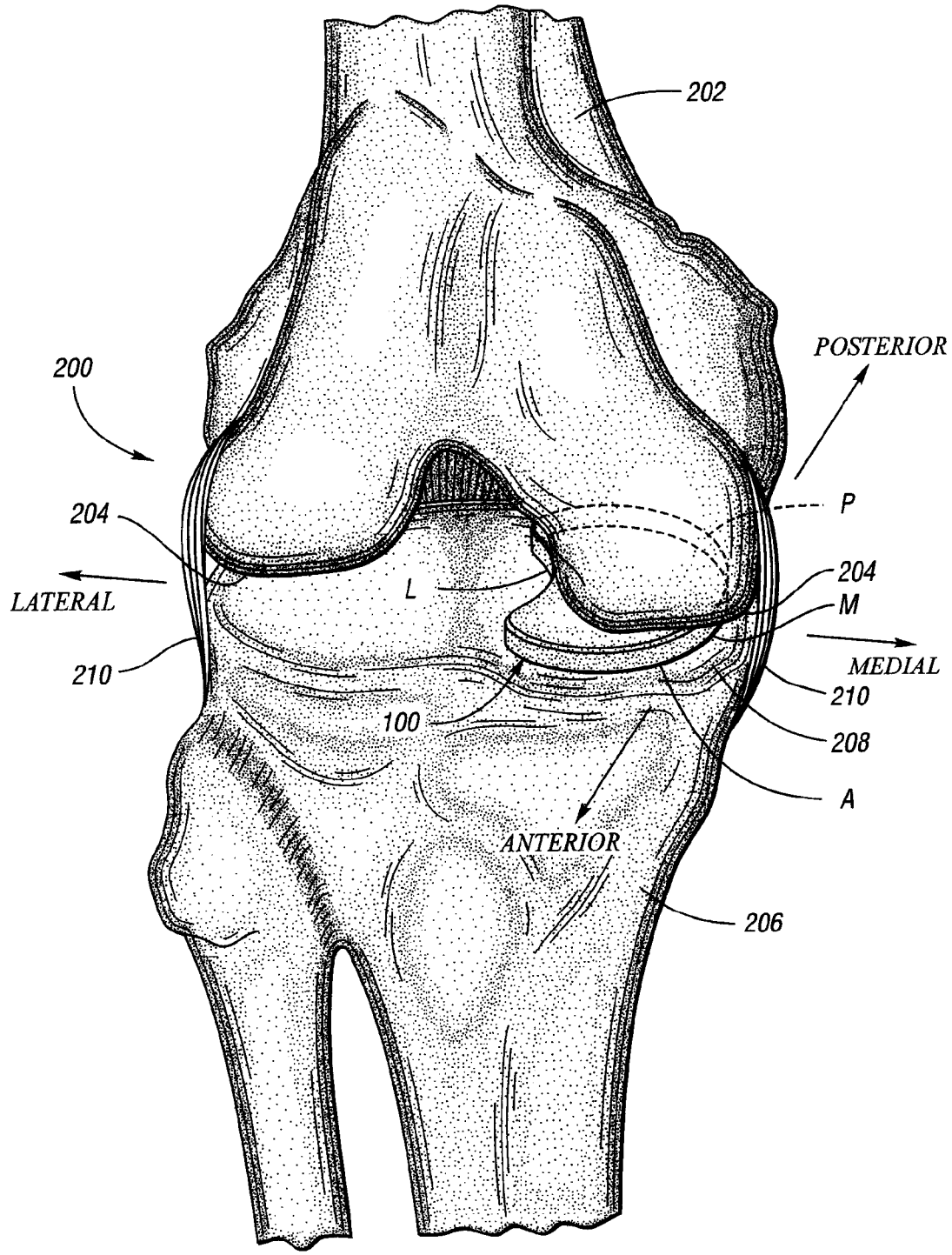
FIG. 5 illustrates placement of the prosthesis in a knee joint.

The present device is an implantable knee prosthesis in the form of a uni-compartmental interpositional spacer which, by effectively replacing worn articular material, restores the normal joint alignment and provides a congruent bearing surface for the femoral condyle to articulate against. Further, it essentially eliminates articulation against the tibial surface thereby preventing further degradation of the tibial surface. Degeneration of the femoral anatomy is significantly reduced because the conforming femoral surface of the device accommodates the complex shape of the femoral condyle in extension as well as in flexion. Insertion of the device is done via a 3 cm to 5 cm medial parapatella incision after arthroscopic debridement of the femoral and tibial cartilage and removal of medial meniscus toward the rim along the anterior, medial and posterior portions. No bone resection or mechanical fixation of the device is required. Only osteophytes which interfere with the device placement or with proper collateral ligament alignment are removed. The device is offered in multiple thicknesses in order to occupy the joint space and tighten the "loose suspenders" problem of the collateral ligaments. By occupying the joint space and retensioning the collateral ligaments, the unicompartmental interpositional spacer improves joint stability and restores the limb to a more normal mechanical alignment.

An implantable knee prosthesis 100 is illustrated in FIG. 1. An anterior/posterior (A/P) cross-sectional view is taken along section line A-A and illustrated in FIG. 2. A medial/lateral (M/L) cross-sectional view is taken along section line B-B and illustrated in FIG. 3. A Coordinate System Origin (CSO) 10 is at the intersection of lines A-A and B-B. Prosthesis 100, FIGS. 1-3, includes a body 102 having a peripheral edge 112, a first or tibial face 104 and a second or femoral face 106.

The current mechanical structure is a compromise between the geometry of the femoral condyle and the kinematics of the knee. Specifically, the femoral condyle has two major AP radii such that when the knee is full extension, one radius position is in contact with the tibial plateau while, during flexion, another portion of the femoral condyle is in contact with the tibial plateau. Further complications arise when it is recognized that the femur rotates with respect to the tibia during flexion, thereby changing the orientation of the femoral anatomy to the tibial plateau. Much study has been dedicated to determine if any relationship exists in the normal human anatomy that would allow one to define the required dimensions of the device for proper fit and function based on a single, easy to establish, measurable anatomic landmark. Based on a study of over 100 MRI's and 75 X-rays of human subjects ranging from 15 to 87 years of age, a relationship was established between the anteroposterior radius of the most distal portion of the femoral condyle and the dimensions which control the geometric form of the device. The database revealed a range of femoral anteroposterior radii from 32 mm to 48 mm. However, it is known that the worldwide range is much larger because of race differences in the human anatomy.

A preferred method of construction aligns the apex of a femoral radius with the CSO 10. FIG. 1. The apex of a tibial surface is also generally aligned in both the A/P and M/L directions with the CSO 10, but is separated vertically from the CSO 10 to create the part thickness. The substantially oval shape of the peripheral edge 112 is then located with respect to the CSO 10. In general, the CSO 10 of the device is located at the center of the ellipse and a minor axis of the ellipse F is related to a major axis D by a ratio ranging from F=0.25 D to 1.5 D with a preferred value of=0.64 D. Similar ratios can be established for all of the controlling dimensions of the part such that the shape in plan i.e., as observed from above or below, femoral surface geometry, and tibial surface geometry for a normal tibial anatomy can generally be defined by one physical A/P measurement of the patient's tibial anatomy. The appropriate thickness of the implant can be determined by measuring the amount of joint space between the femoral and tibial surface when a minor amount of valgus (heels out, knees in) is applied to the knee.

Referring again to FIGS. 1-3, the preferred relationship between femoral radius RA to other joint dimensions (femoral radius is the driving radius to all other dimensions) is as follows:

Medial-lateral radius RB=0.25 A to 1.0 A
Curve of anterior half of Femoral Radius RC=0.5 A to 2.0 A, Posterior half is straight
Length D=0.6 A to 1.4 A
Posterior half E=0.1 A to 0.75 A
Width F=0.25 A to 1.5 A
Width from part center to medial edge G=0.096 A to 0.48 A
Anterior plan radius RH=0.16 A to 0.64 A
Posterior plan radius RM=0.16 A to 0.64 A
Radius along lateral spine area RP=0.1 A to 2.0 A
Width from part center to lateral edge Q=−0.32 A to +0.32 A
Location of transition from anterior radius to medial radius Y=−0.32 A to +0.32 A (a negative value means that a dimension may extend to an opposite side of section line A-A).

Below are the preferred ratios used to define the shape of prosthesis 100 in terms of the dimension RA, i.e. the femoral radius of prosthesis 100.

P=0.238 A
E=0.5 A
F=0.64 A
H=0.32 A
M=0.384 A
G=0.352 A
Q=0.1056 A
Y=0.1152 A
B=0.68 A
D=RA
RC=RA

The actual shape of the present device may be tailored to the individual. Individuals with high varus or valgus deformation due to wear, degeneration, or disease, may require a device which is of considerably greater thickness over the portions where wear is most advanced. In youthful patients, where trauma-induced damage rather than severe wear or degeneration has occurred, differences in device thickness will be more moderate. In general, the device is kidney-shaped when viewed in plan, and has a negative meniscus shape when viewed from the side, i.e.; the thickness along the periphery of the device being greater than the thickness along the center of the device. The kidney-shape in plan may be described generally as elliptical, the shape resembling a distorted ellipse.

One skilled in the art can approximate the generally elliptical shape with a combination of straight lines and radial blends. Therefore, the term "substantially elliptical" is intended to include all construction methods which yield a planar shape which is longer in one direction than the transverse direction, and has rounded corners.

For example, in one of the embodiments of FIGS. 4a-4d, the implantable knee prosthesis 100 comprises body 102 having a generally elliptical shape in plan including the first face 104 and the opposite second face 106. The first face 104 is substantially kidney shaped in plan and the second face 106 is substantially kidney shaped in plan. The first face 104 includes a convex surface 108. The second face 106 includes a concave surface 110. The first face 104 includes a contour (discussed above) which is substantially the same as an associated contour of the tibial plateau. The second face 106 includes a contour (discussed above) which is substantially the same as an associated contour of the femoral condyle in extension.

A peripheral edge 112 extends between the first face 104 and the second face 106 and includes a first or medial side M, a second or lateral side L, opposite the first side M, a first or anterior end A and a second or posterior end P opposite the first end A.

The second or lateral side L includes a pair of lobes 122a and 122b. The lobe 122a is adjacent the anterior end A of body 102 and the lobe 122b is adjacent the posterior end P of body 102. A notch 124 is preferably formed between the lobes 122a, 122b so that the lobes 122a, 122b are spaced apart by the notch 124.

As illustrated in FIGS. 1 and 4a-4d, a dimension D, in a range of from about 0.6 A to about 1.4 A, is defined by the first end A and the second end P. Another dimension F is defined by the lobes 122a, 122b of first side M and the second side L. It has been found that a suitable size for body 102 is defined by the dimension F being from about 0.25 A to about 1.5 A of the dimension D. Also a dimension E extends from the CSO 10 of the body 102 to the first end A. It has also been found that a suitable size for body 102 is also defined by the dimension E being from about 0.1 A to about 0.75 A of the dimension D. Further, a dimension G extends substantially from the CSO 10 of body 102 to the first side M. It has further been found that a suitable size for body 102 is further defined by the dimension G being from about 0.096 A to about 0.48 A of the dimension F.

In FIG. 5, prosthesis 100 is positioned in a knee joint 200 between a femur 202, including the femoral condyles 204, and a tibia 206 including the tibial plateau 208. The femur 202 and tibia 206 include interconnecting collateral ligaments 210. The device 100 illustrates the position of the posterior end P, the anterior end A, the medial side M and the lateral side L when the device 100 is inserted in the knee joint 200.

The prosthetic device of the subject invention is a unicompartmental device suitable for minimally invasive, surgical implantation without requiring bone resection. The device is positioned within a compartment in which a portion of the natural meniscus is ordinarily located. The natural meniscus may be maintained in position or may be wholly or partially removed, depending upon its condition. Under ordinary circumstances, pieces of the natural meniscus which have been torn away are removed, and damaged areas may be trimmed as necessary. In somewhat rarer instances, the entire portion of the meniscus residing in the meniscal cavity may be removed. Actually, as described hereinafter, the shape of the present device is not the same as the natural meniscus, and in most cases, will not entirely replace the meniscus.

By the term "unicompartmental" is meant that each device is suitable for implantation into but one compartment defined by the space between a femoral condyle and its associated tibial plateau. In other words, the present device is not a "bicompartmental" device which, in one rigid device, could be inserted into both of the femoral condyle/tibial plateau compartments. In many, if not most cases, a device will be inserted into one compartment only, generally the medial compartment, as the meniscus and associated articular surfaces in these compartments (left knee medial and right knee medial compartments) are most subject to wear and damage. However, it is possible to insert two separate devices into the medial and lateral compartments of the same knee, or to use two such devices that are mechanically but non-rigidly linked.

The present device is translatable but self-centering. By "translatable" is meant that during natural articulation of the knee joint, the device is allowed to move, or change its position. Thus, the present device is devoid of means of physical attachment which limit its movement (for example, screws, mating ridges and depressions, porous areas to accommodate tissue regrowth, and the like).

The term "self-centering" means that upon translation from a first position to a second position during knee articulation, the device will return to substantially its original position as the articulation of the knee joint is reversed and the original knee position is reached. Thus, the device will not progressively "creep" toward one side of the compartment in which it is located. Rather, the angle of attack of the femoral condyle and/or tibial plateau bearing surfaces against the device will ensure that the device reversibly translates during articulation, maintaining the device, on average, in the same location for any given degree of knee articulation. The centered, rest position, of the implant is usually determined when the knee is in extension and there is maximum contact between the femoral condyle and the device. This ability of the device to "self-center" can be compromised by inadequate tension of either one or both of the cruciate ligaments. Unbalanced or excessive cruciate ligament tension can possibly cause the device to locate itself in a more anterior position on the tibia, which is less desirable.

Contrary to most devices which are composed of soft, compliant material designed to assume the function of the natural meniscus which they replace, the present device is composed of relatively hard, relatively high modulus material. Suitable materials are, for example, steel, ceramics, and reinforced and nonreinforced thermoset or thermoplastic polymers. The device need not be made of a single material, but composite structures of steel/thermoplastic, steel/ceramic, ceramic/polymer, etc., may be used. Alternatively, composites of the above materials with biologically active surfaces or components may be used. Biologically active components include surfaces that may contain pharmaceutical agents to stimulate cartilage growth or retard cartilage degeneration that may be delivered at once or in a timed-release manner.

Generally, portions of the device expected to have the most wear due to either greater movement relative to the mating surface (i.e., relative to the femoral condyle or tibial plateau) or high stress, may be made of stronger, more abrasion resistant material than the remainder of the device when composite structures are used. This method may be ideal for use in conjunction with cultured chondrocyte implantation (cartilage cells used as seeds) or osteochondral transplantation. Moreover, when the locus of damage to the articular cartilage or to a portion of the bone structure are known, the relatively constant radius of the surface of the present device will bridge the defective areas at these loci, thus redistributing load to healthy tissue and allowing inflamed, diseased, or other damaged areas to regenerate.

For example, a portion of the femoral condyle, tibial plateau, articular cartilage, etc., may have been damaged or may experience tissue degeneration. The continued load experienced at such points and the wear experienced as the knee flexes will substantially hinder the regeneration of healthy tissue. If suitable biologically active materials, chondrocytes, etc. are applied to the damaged or degenerated surface to assist in tissue regeneration, these will, under ordinary circumstances, be rapidly dissipated. If a flexible, cushiony material is inserted within the knee compartment, the damaged area will still experience intimate contact with the damaged area under static loads, and will also experience continued wear and abrasion under non-static conditions. Under such circumstances, active substances will be rapidly dissipated. However, more importantly, newly regenerated articular cartilage not having the necessary density or cohesiveness to withstand wear, will be rapidly eroded away.

The present device may be supplied with a contoured surface which distributes the loads evenly over regions of healthy articular cartilage while bridging areas where articular cartilage degeneration or damage has occurred. Active substances may be applied at once or in a timed-release manner to the degenerated or damaged articular cartilage surface by means of, or in conjunction with, the present device. Because the recess or shape of the device protects the damaged area from loads and wear, tissue regeneration may occur without disturbance. The regenerating tissue will have time to mature and crossline into a fully developed matrix. Moreover, as regeneration proceeds, the regenerating tissue will assume a shape dictated by the shape of the device. Growth under these circumstances has the greatest potential for dense, ordered cartilage most closely replicating the original surface.

The hardness of the present device is preferably higher than Shore 60 D. The Shore hardness may range from that common for engineering grade plastics to hardened steel and titanium, and preferably on the portion of the Rockwell hardness scale typical of steels, hard plastics and ceramic materials. From the high hardness desired of the device, it is readily apparent that the device functions in a manner completely different from those of the prior art. The purpose of the device of the subject invention is to achieve a span-like effect to bridge the defective areas. However, in a composite variation, any single component (like a bioactive material component) may be softer than the supporting material. Rather than deforming to distribute a load relatively equally on the mating surfaces, the device of the present invention functions as a rigid, substantially non-deforming, self-centering bearing, which does not necessarily spread the load uniformly, but rather may concentrate the load upon desired points, spanning areas of imperfection. If a soft and/or low modulus elastomer or thermoplastic is used for the entire device, not only is the load not concentrated on healthy tissue, but damaged areas will also be subjected to loading, thereby decreasing the opportunity for the body's natural regenerative capability to function.

The high modulus of the present device thus allows for the provision of recessed or non-contacting areas of the device to encourage articular cartilage regeneration. In softer, lower modulus materials, the naturally occurring loads, which may exceed 1000 lbs/in$^2$, in certain cases, will cause the softer devices to deform and allow ordinarily non-contacting areas to contact bone or cartilage for which contact is not desired. A flexural modulus of elasticity for load bearing portions of the present device should therefore be preferably greater than $2\times10^5$ psi, and more preferably greater than $3\times10^6$ psi. Portions of the device not exposed to the highest loads may be made of lower modulus materials, which may be softer as well (e.g., in a non-limiting sense, nylon, polyurethane, polypropylene, polyester, and the like, optionally fiber reinforced).

As indicated previously, the device of the subject invention may be manufactured so as to substantially contain or have deposited thereon, a biologically or pharmaceutically active material. This is particularly suitable when the device bridges a defective area of bone or articular cartilage. In such cases, the device may be provided with a coating containing a biologically or pharmaceutically active material, for example one that promotes tissue regrowth or one that decreases inflammation. Such materials may also, and more preferably, be contained in a portion of the meniscal device. The portion may be filled with medication, or may be filled with a gel, paste, or soft polymer material that releases medication over a period of time. Preferably, this medically active portion does not actually contact, or minimally contacts, the damaged tissue. This freedom from contact is made possible by the surrounding bearing surfaces. Coatings may also be of a gel, paste, or polymer containing time-release medicaments. Biologically and pharmaceutically active materials are identified subsequently herein as "active materials."

The edges of the device are rounded rather than presenting the sharp corners of the devices of U.S. Pat. No. 5,158,574. This rounded periphery is necessary due to the fact that the device will be allowed to move within the cavity. Movement of a device having a periphery with sharp corners would result in the potential for severe damage to the surrounding tissue and articular surfaces, in addition to causing pain. A "depression" in the elliptical shape on the part of the device which will be proximate to the tibial spine will vary from patient to patient. It is possible due to the great range of variability of human anatomy that this depression might be absent in devices for some patients. However, the overall shape in plan is substantially elliptical regardless.

The axis of rotation of the tibia on the femur is 90 degrees to the path of the tibial plateau against the femoral condyle. The two tibial plateaus (medial and lateral) are not in the same plane with each other but do act in a relatively constant radius to its respective femoral condyle. In other words, although the symmetry of the device's femoral side may be matched with the femoral condyle while the leg is in full extension, the rotation of the tibial plateau against the femoral condyle is along a constant axis of rotation (90 degrees to the axis of rotation), thus the angularity of the axis of symmetry of the femoral condyle relative to the axis of symmetry of the tibial plateau is not parallel but at some acute angle. Also, the axis of symmetry of the tibial plateau is not parallel to the path of rotation of the tibia relative to the femur but also at some mildly acute angle. Thus, the true orientation of the device, regardless of the relative orientations of symmetry of the tibial side to the femoral side is 90 degrees to the true axis of rotation as described in Hollister et al., "The Axes of Rotation of the Knee", Clin. Orthopaedics and Rel. Res., 290 pp. 259-268, J.B. Lippincott Co., 1993, herein incorporated by reference. Any localized positions of higher loads are self-limiting due to the ability of the device to translate both rotationally and laterally which mimics the true motion of the natural meniscus as described by Hollister.

During the load bearing portion of the gait cycle, or stance phase, flexion at the knee does not typically exceed 35°. Thus, the highest compressive loads in the knee occur with the knee substantially extended. The outer contours of the device are therefore designed to substantially mate with the corresponding tibial and femoral surfaces when the knee is in full extension so that the high compressive loads can be distributed over large surface areas. The contact areas between the femoral condyle and the femoral surface of the device, and the tibial plateau and the tibial surface of the device are substantially equivalent during extension. However, because the contour of the femoral surface is more concave, the femoral condyle determines the position of the device on the surface of the tibial plateau in extension.

As the knee is flexed, the mating along the tibial surface is substantially maintained. However, the contoured mating surfaces of the femoral condyle and femoral surfaces of the present device can become increasingly dissimilar when the joint articulates. As the knee is flexed, there is a relative external rotation and posterior translation of the femur with respect to the tibia. Thus, the contour angle of the femur becomes more in-line with the contour angle of the tibia in flexion. This can cause relative lateral or rotational movement, in the tibial plane, between the femoral condyle and the femoral surface of the device. The forces generated by the increasingly different geometry creates a rotational moment, in the tibial plane, which is resisted along the mating tibial surfaces and which also results in a restoring force tending to correctly locate the device along the femoral condyle. Thus, the device is self-centering to the femoral condyle, in part, as a result of the conformity between the femoral condyle and the femoral surface of the device.

By changing the femoral surface of the implant, it is possible to reduce the rotational moment induced during flexion by the mismatch between the femoral surface of the implant and the femoral condyle. A preferred method to accommodate this motion is to have a less acute alignment between the femoral and tibial axes of symmetry posterior to the A/P midline, thereby reducing the mismatch between the two axes in flexion. This angle is preferably 0° and can range from ±10°. Anterior to the midline, the femoral contour is bent around a radius RC that is tangent to the posterior section of the sweep plane at the most distal point of the femoral A/P radius RA. This femoral surface geometry is essentially a compromise between the different extension and flexion alignments of the femoral and tibial axes of symmetry.

Because the device has no physical method of attachment, the combination of the slightly concave tibial surface and the convex femoral surface serves to locate the device though all ranges of motion provided that the collateral ligaments are in proper tension. If too thin, a device could be ejected from the knee compartment. By the very nature of the ability to adjust for the lost articular material through the thickness of the device, the thickness adjustment substantially eliminates the need for a functional meniscus as a bearing surface in a severely (Grade III or IV) degenerated knee. In these instances, the femoral surface of the device resides significantly above the meniscal edge, and the meniscus is completely unloaded.

The device also increases the translational stability of the knee. The conforming shape of the femoral surface limits excessive anterior to posterior translation of the femur. As a result, this device possibly eliminates the need for ACL reconstruction in the older patient.

Figures 6, 7:
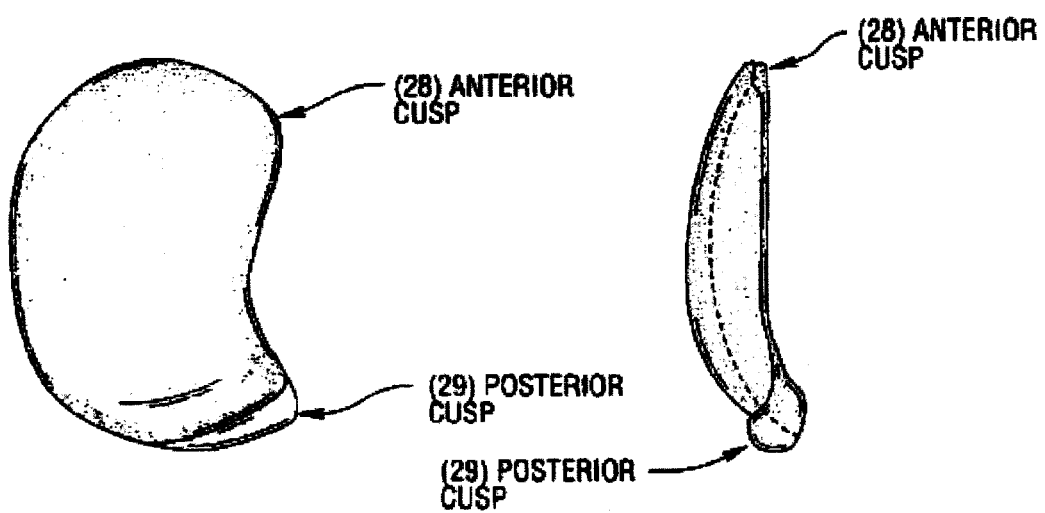
FIG. 6 is a top plan view of a prosthesis including anterior and posterior cusps according to an aspect of the present invention.
FIG. 7 is a side elevational view of the prosthesis of FIG. 6.

In some cases is may be necessary to add "reverse (downward)" curves, or cusps, to prosthesis 100 as shown in FIGS. 6 and 7, located along the lateral aspect (of a medial device) of the device at the extreme anterior/lateral 28 and posterior/lateral protrusions 29. Such circumstances would be when there is deformed anatomy or additional stabilization is required of prosthesis 100.

Generally speaking, each knee presents a different geometry of the respective femoral condyles and tibial plateaus. Even with respect to the right and left knees of a single individual, although bilateral symmetry dictates that the left and right knee components should be mirror images, this is often only an approximation. Thus, the shape of the affected femoral condyle and tibial plateau (while discussed herein in the singular, more than one pair of condyle(s)/plateau(s) may be involved), will have to be ascertained to determine the correct geometry of the device for a given patient.

To implant a device that possesses the characteristics required by the subject invention, the patient's knee joint may be examined by a non-invasive imaging procedure capable of generating sufficient information such that one appropriately sized and shaped device may be selected. While a variety of non-invasive imaging devices may be suitable, for example X-ray devices and the like, it is preferable that information as to the size and shape of the device be provided by magnetic resonance imaging (MRI).

Two methods of non-invasive imaging for selection of a suitable prosthesis are preferred. In the first method, MRI or other non-invasive imaging scans, optionally coupled with exterior measurements of the dimensions of the relevant tibial and femoral portions including the surface of the particular cartilage of the tibia and femur, may be used to establish a library of prostheses whose size and geometry differ according to the age and size of the patient, the patient's genetic make-up, and the like. A limited number of "standard" devices are then made to meet the requirements of a generic population of patients.

In this first method, a non-invasive imaging scan, such as X-ray or MRI, together with knowledge of the patient's genetic make-up, general body type, extent of the disease, degeneration, or trauma and the like, will enable the surgeon to select a device of the correct size and shape from the library for the patient. The device is then introduced by arthroscopically assisted implantation, generally limited to extensive clean-up of existing damaged tissue, e.g., torn or particulate natural meniscus damage. It may also be used in conjunction with tibial osteotomy or articular surfacing procedure such as cartilage transplantations or abrasion anthroplasty. Following insertion of the device, X-ray, Fluoroscopy, or MRI may be used to assess the correct positioning of the device both introperatively as well as postoperatively. Because the surgical procedures used are not severe, and also not irreversible, an unsuitable device may be readily removed and replaced, either with a different device from a device library, or by a custom device.

In a second method, each patient receives one or more devices that are custom tailored for the individual by producing a contour plot of the femoral and tibial mating surfaces and the size of the meniscal cavity. Such a contour plot may be constructed from imaging data, i.e. MRI data, by a suitable computer program. From the contour plot, the correct surface geometry of the device is determined from the shape of the respective tibial plateau and femoral condyle and the orientation between the two surfaces in extension. In general, the shapes just mentioned also include the articular cartilage, which, in general, is maintained substantially intact.

In accordance with this invention it has been discovered that the amount of varus deformity is the primary, non-invasive method for determining the necessary device thickness required for proper functioning of the device. Viewing a weight bearing anteroposterior X-ray, a cut and paste of a line drawn through the femoral condyles and repositioned to put them once again parallel to the tibial plateaus will yield a measurement for the approximate device thickness.

A further understanding can be obtained by reference to the following specific example that is provided herein for purposes of illustration only and is not intended to be limiting unless otherwise specified.

For Example:

A 44-year-old male had an 18-degree flexion contracture in his right knee. The right limb was in 5 degrees of varus alignment and the patient suffered from significant, debilitating pain. X-rays of the affected limb showed significant collapse of the medial joint space as well as significant osteophyte formation along the medial border of the femoral condyle. Pre-operative templating of the X-ray indicated that the right medial condyle had a radius of approximately 46 mm. A library of implants was manufactured for this patient based upon the preoperative radius measurement and the dimensional relationships established from the X-ray and MRI database. The library included implants with a femoral radius measuring 42 mm, 46 mm and 50 mm. Implants of 2 mm, 3 mm and 4 mm thickness were made in each size category. The patient was then scheduled for surgery.

Arthroscopic evaluation of the joint on the day of surgery revealed generalized Grade III chondromalicia of the medial femoral condyle and tibial plateau with small areas of Grade IV changes. Patellofemoral and lateral joint compartment changes were mild. An arthroscopic debridement of the joint was completed and the degenerated edge of the meniscus was resected. A small ruler was inserted through the anterior arthroscopic portal and the distance from the posterior rim to the anterior rim of the remaining meniscus was recorded as 42 mm. A short median parapatellar incision was completed to expose the medial compartment of the knee. An osteotome and a rongure were used to remove the osteophytes along the medial border of the femoral condyle. Plastic gages representing the different implant thicknesses were then inserted between the femur and the tibia to measure the amount of joint space present in the medial compartment. These measurements indicated that a 4 mm thick part would be required to occupy the joint space and restore tension to the medial compartment. Several trial implants were inserted into the joint space and a fluoroscope was used to verify the fit and positioning of each trial. This final trial reduction confirmed that the appropriate part was a 42 mm long by 4 mm thick implant. The implant was inserted into the joint. A final check of the implant's stability and fit was performed. Careful attention was paid to the evaluation of implant thickness because an inappropriately thick implant could prevent the patient from achieving full extension. After all interoperative checks were complete the incision was closed.

Postoperative X-rays revealed a 7-degree correction of the limb alignment. The implant also stabilized the knee. At 10 months of follow-up the patient is pain free and can achieve full knee extension. The patient can also achieve approximately 120 degrees of flexion.

One preferred surgical procedure which may be used to implant this device can be described by the following steps:
1. Verify preoperative indications:
   a. Varus determination of <5 degrees with erect AP X-ray;
   b. Medial compartment disease only. Some lateral spurs may be present; and
   c. Pre-operative sizing via M/L template measurement of A/P X-ray.
2. Standard Arthroscopy surgical prep:
   a. Infiltrate knee with Lidocaine/Marcaine and Epinephine.
3. Arthroscopy:
   a. Inspect lateral patello-femoral compartments for integrity, some mild arthrosis is acceptable;
   b. Removal of medial meniscus toward the rim along the anterior, medial and posterior portions;
   c. Initial arthroscopic osteophyte removal via ⅛" osteotome and burr to allow for valgus positioning of the knee;
   d. Complete the removal (to the rim) of the posterior and posterior-lateral meniscus; and
   e. Confirm sizing of the device by measuring distance from resected posterior meniscus to remaining anterior meniscus.
4. Medial parapatellar arthrotomy (mid-patella to tibial joint line).
5. Complete removal of visible osteophytes along the medial femoral condyle.
6. Insert thickness gauge and size for implant thickness.
7. Insert trial component:
   a. Flex knee to approximately 50+ degrees to fully expose the distal portion of the femoral condyle;
   b. Insert trial component; and
   c. While applying insertion pressure, apply valgus stress to the tibia and "stretch-extend" the tibia over the trial component.
8. Check for proper sizing with "true lateral" and A/P fluoroscope images of the knee while in extension:
   a. Ideally, the device should be within 1 mm of the A/P boundries of the tibial plateau and superimposed over the medial boundary.
9. Remove trial component and flush joint with saline.
10. Insert the appropriate implant.
11. Confirm proper placement and sizing with fluoroscopic images as with trial component.
12. Maintain leg in extension and close wound after insertion of a Hemovac drain.
13. Place leg in immobilizer prior to patient transfer.

Having now fully described the invention, it will be apparent to one of ordinary skill in the art that many changes and modifications can be made thereto without departing from the spirit or scope of the invention as set forth herein.

What is claimed is:

1. A unicompartmental knee prosthesis for implantation into a knee joint compartment between a femoral condyle and its corresponding tibial plateau, the prosthesis comprising:
   a body having a substantially elliptical shape in plan and a pair of contoured opposed faces including a first face and a second face, the first face including a convex surface comprising substantially an entirety of the first face and the second face including a concave surface, the prosthesis free of fixation to a permanent location within the knee joint compartment and configured to be translatable with respect to the tibial plateau during knee articulation;
   a peripheral edge extending between the faces and having a first side, a second side opposite the first side, a first end and a second end opposite the first end, the body including a cusp comprising a reverse downward curve with respect to the first face protruding from at least one of the first and second ends for limiting translation of the prosthesis;
   a first dimension D defined by the first end and the second end;
   a second dimension F defined by the first side and the second side, and
   a coordinate system origin (CSO) at an intersection of D and F, the body including a material thickness at the CSO, where the dimension F is from about 0.25 to about 1.5 of the dimension D,
   wherein the prosthesis is implantable without requiring bone resection.

2. The prosthesis according to claim 1 wherein the second face includes an anterior to posterior radius A and the first dimension D, where D is from about 0.6 A to about 1.4 A.

3. The prosthesis according to claim 2 wherein the anterior to posterior radius A is equal to the first dimension D.

4. The prosthesis according to claim 2 wherein the second dimension F is 0.64 A.

5. The prosthesis according to claim 2 wherein the second face includes a medial to lateral radius B of from about 0.25 A to about 1.0 A.

6. The prosthesis according to claim 5 wherein the radius B is 0.68 A.

7. The prosthesis according to claim 2 further comprising:
   a posterior portion; and
   a posterior portion dimension E of from about 0.1 A to about 0.75 A.

8. The prosthesis according to claim 7 wherein the posterior portion dimension E=0.5 A.

9. The prosthesis according to claim 2 further comprising:
   a part center location;
   a medial edge; and
   a width from part center location to medial edge dimension G of from about 0.096 A to about 0.48 A.

10. The prosthesis according to claim 9 wherein the width from part center location to medial edge dimension G=0.352 A.

11. The prosthesis according to claim 2 further comprising:
    a posterior portion;
    a posterior portion dimension E of from about 0.1 A to about 0.75 A;
    a part center location;
    a medial edge; and
    a width from part center location to medial edge dimension G of from about 0.096 A to about 0.48 A.

12. The prosthesis according to claim 11 wherein the posterior portion dimension E=0.5 A and the width from part center location to medial edge dimension G=0.352 A.

13. The prosthesis according to claim 2 wherein the second face includes an anterior sweep radius C to accommodate relative rotation between the femoral condyle and the tibial plateau.

14. The prosthesis according to claim 13 wherein C is from about 0.5 A to about 2.0 A.

15. The prosthesis according to claim 14 wherein C=A.

* * * * *